US005955299A

United States Patent [19]
Hillman et al.

[11] Patent Number: 5,955,299
[45] Date of Patent: Sep. 21, 1999

[54] SNRNP SM PROTEINS

[75] Inventors: Jennifer L. Hillman, San Jose; Olga Bandman, Mountain; Gary B. Zweiger, San Mateo, all of Calif.

[73] Assignee: Incyte Pharmaceuticals, Inc., Palo Alto, Calif.

[21] Appl. No.: 08/722,349

[22] Filed: Sep. 27, 1996

[51] Int. Cl.$^6$ .............................. C12P 21/02; C12N 1/21; C12N 15/63; C07H 21/04
[52] U.S. Cl. .................. 435/69.1; 435/252.3; 435/320.1; 536/23.5
[58] Field of Search ................................ 435/69.1, 320.1, 435/252.3; 536/23.5

[56] References Cited

PUBLICATIONS

Lerner, M.R., et al., "Antibodies to small nuclear RNAs complexed with proteins are produced by patients with systemic lupus erythematosus", *Proc. Natl. Acad. Sci.*, 76:5495–5499 (1979).

Raker, V.A., et al., "The snRNP core assembly pathway: identification of stable core protein heteromeric complexes and an snRNP subcore particle in vitro", *EMBO J.*, 15:2256–2269 (1996).

Seraphin, B., "Sm and Sm–like proteins belong to a large family: identification of proteins of the U6 as well as the U1, U2, U4 and U5 snRNPs", *EMBO J.*, 14:2089–2098 (1995).

Wilson, R., et al., "2.2 Mb of contiguous nucleotide sequence from chromosome III of C. elegans", *Nature*, 368:32–38 (1994).

Van Dyck, L., et al., "Analysis of a 17.4 kb DNA Segment of Yeast Chromosome II Encompassing the Ribosomal Protein L19 as well as Proteins with Homologies to Components of the hnRNP and snRNP Complexes and to the Human Proliferation–associated p120 Antigen", *Yeast*, 10:1663–1673 (1994).

Tomer, Y., et al., "Pathogenic Significance and Diagnostic Value of Lupus Autoantibodies", *Int Arch Allergy Immunol*, 100:293–306 (1993).

Grgacic, E., et al., "Cell–mediated immune response to copolymer I in multiple sclerosis measured by the macrophage procoagulant activity assay", *Int. Immunol*, 2:713–718 (1990).

Teitelbaum, D., et al., "Copolymer 1 inhibits chronic relapsing experimental allergic encephalomyelitis induced by proteolipid protein (PLP) peptides in mice and interferes with PLP–specific T cell responses", *J. Neuro.*, 64:209–217 (1996).

Mallet, L., (GI 1078051), GenBank Sequence Database (Accession 1078051), 1995, National Center for Biotechnology Information, National Library of Medicine, Bethesda, Maryland 20894.

Hermann, H. et al. "snRNP Sm protein share two evolutionarily conserved sequence motifs which are involved in Sm protein–protein interactions" EMBO Journal (May, 1995), vol. 14, No. 9, pp. 2076–2088.

Rokeach, L.A. et al. "Molecular cloning of a cDNA encoding the human Sm–D autoantigen" Proceedings of the National Academy of Sciences, USA (Jul., 1988), vol. 85, pp. 4832–4836.

Wagatsuma, M. et al. "Antibody recognition of the recombinant human nuclear antigens RNP 70kD, SS–A, SS–B, Sm–B and Sm–D by autoimmune sera" Molecular Immunology (Nov., 1993), vol. 30, No. 16, pp. 1491–1498.

*Primary Examiner*—Kawai Lau
*Attorney, Agent, or Firm*—Lucy J. Billings; Incyte Pharmaceuticals, Inc.

[57] ABSTRACT

The present invention provides novel human small nuclear ribonucleoprotein (snRNP) Sm proteins (collectively called HSMP) and polynucleotides which identify and encode HSMP. The invention also provides genetically engineered expression vectors and host cells comprising the nucleic acid sequences encoding HSMP. The invention also provides pharmaceutical compositions containing HSMP or antagonists to HSMP, and in the use of these compositions for the treatment of diseases associated with the expression of HSMP. Additionally, the invention provides for the use of antisense molecules to polynucleotides encoding HSMP for the treatment of diseases associated with the expression of HSMP. The invention also provides diagnostic assays which utilize the polynucleotide, or fragments or the complement thereof, to hybridize to the genomic sequence or transcripts of polynucleotides encoding HSMP or anti-HSMP antibodies which specifically bind to HSMP.

12 Claims, 8 Drawing Sheets

```
                    9              18              27              36              45              54
5' CGG CTC GAG GCC ACA CGG CGC GAC AAG ATG GCG GAT AAG GAG AAG AAG AAA AAG
                                         M   A   D   K   E   K   K   K   K 63              72              81              90              99              108
GAG AGC ATC TTG GAC TTG TCC AAG TAC ATC GAC AAG ACG ATC CGG GTA AAG TTC
 E   S   I   L   D   L   S   K   Y   I   D   K   T   I   R   V   K   F 117             126             135             144             153             162
CAG GGA GGC CGC GAA GCC AGT GGA ATC CTG AAG GGC TTC GAC CCA CTC CTC AAC
 Q   G   G   R   E   A   S   G   I   L   K   G   F   D   P   L   L   N 171             180             189             198             207             216
CTT GTG CTG GAC GGC ACC ATT GAG TAC ATG CGA GAC CCT GAC GAC CAG TAC AAG
 L   V   L   D   G   T   I   E   Y   M   R   D   P   D   D   Q   Y   K 225             234             243             252             261             270
CTC ACG GAG GAC ACC CGG CAG CTG GGC CTC GTG GTG TGC CGG GGC ACG TCC GTG
 L   T   E   D   T   R   Q   L   G   L   V   V   C   R   G   T   S   V 279             288             297             306             315             324
GTG CTA ATC TGC CCG CAG GAC GGC ATG GAG GCC ATC CCC AAC CCC TTC ATC CAG
 V   L   I   C   P   Q   D   G   M   E   A   I   P   N   P   F   I   Q 333             342             351             360             369             378
CAG CAG GAC GCC TAG CCT GGC CGG GGG CGC GGG GGG TGC AGG GCA GGC CCG AGC
 Q   Q   D   A 387             396             405             414             423             432
AGC TCG GTT TCC CGC GGA CTT GGC TGC TGC TCC CAC CGC AGT ACC GCC TCC TGG 441             450             459             468             477             486
AAC GGA AGC ATT TTC CTT TTT GTA TAG GTT GAA TTT TTG TTT TCT TAA TAA AAT

495
TGC AAA CCT CAA  3'
```

FIGURE 1

```
              9              18              27              36              45              54
5' TAC TCT ACC CAG CTT GCG CTC CCC AGC CGC AAG TNG GCC GCG CTT TGC CCG TCA 63             72              81              90              99             108
   GCG CTT GGA GCT TTC TGC GTC GCT TCC CGC TGC GCC TGC GCG GTC CCG CCT CGY 117            126             135             144             153             162
   CCC ACG CGC GGG CTC GCG CTT CGG TTT CCC CAG ACC TGC TCG CAG CAC CCT GCT 171            180             189             198             207             216
   GTC TTC CCG GTC CGG CCC GCT GCC CGC GGC GCC AGC ACC ATG CTC TTC TAT TCT
                                                               M   L   F   Y   S 225            234             243             252             261             270
   TTT TTC AAG TCC CTT GTG GGC AAG GAT GTG GTC GTG GAA CTA AAG AAT GAC CTG
    F   F   K   S   L   V   G   K   D   V   V   V   E   L   K   N   D   L 279            288             297             306             315             324
   AGC ATC TGT GGA ACC CTC CAT TCT GTG GAT CAG TAT CTC AAC ATC AAA CTA ACT
    S   I   C   G   T   L   H   S   V   D   Q   Y   L   N   I   K   L   T 333            342             351             360             369             378
   GAC ATC AGT GTC ACA GAC CCT GAG AAA TAC CCT CAC ATG TTA TCA GTG AAG AAC
    D   I   S   V   T   D   P   E   K   Y   P   H   M   L   S   V   K   N 387            396             405             414             423             432
   TGC TTC ATT CGG GGC TCA GTG GTC CGA TAC GTG CAG CTG CCA GCA GAT GAG GTC
    C   F   I   R   G   S   V   V   R   Y   V   Q   L   P   A   D   E   V 441            450             459             468             477             486
   GAC ACA CAG TTG CTA CAG GAT GCG GCA AGG AAG GAA GCC CTG CAG CAG AAA CAG
    D   T   Q   L   L   Q   D   A   A   R   K   E   A   L   Q   Q   K   Q 495            504             513             522             531             540
   TGA TGG CTC CTT CTC TTT TCC CTC CCT TTC ATT GGT GAC CCA TAA CCC CAA GTC 549            558             567             576             585             594
   CCA GCC CAG AAC CCC TAA CCC CCA ATA CTT GAA GGG GTT TTG TTT TTT TAC TAA 603            612             621             630             639             648
   TGA TGG TTT TGT GGG TTT TTT TTA AGG GAT GAG TGG ATG AGA GGA GTA ATA GGG 657            666             675             684             693             702
   AAC AGC TAT CCT CTC TTG AGA AGG GGA GGA TAA GTA GGC TGG GAA ACT TCA AAG 711            720
   CCT TCC CAG TCC CCA GCA   3'
```

FIGURE 2

```
1   M A D K E - K K K K - - - - - - E S I L D L S K Y I D K T I   SEQ ID NO-1
1   M S K D E G K R K K - - - - - - E S V V D L T R F L D K E I   SEQ ID NO-5
1   M H Q Q H S Q R K K F E G P K R E A I L D L A K Y K D S K I   SEQ ID NO-6
1   M S K A H P P - - - - - - - - - - - - E L K K F M D K K L   SEQ ID NO-7

24  R V K F Q G G R E A S G I L K G F D P L L N L V L D G T I E   SEQ ID NO-1
25  R V K F Q G G R E A S G V L R G F D Q L L N M V L D D C R E   SEQ ID NO-5
31  R V K L M G G K L V I G V L K G Y D Q L M N L V L D D T V E   SEQ ID NO-6
18  S L K L N G G R H V Q G I L R G F D P F M N L V I D E C V E   SEQ ID NO-7

54  Y M R D P D D Q Y K - - - L T E D T R Q L G L V V C R G T S   SEQ ID NO-1
55  Y L R D P Q N P S V - - - V G D E T R Q L G L I V A R G T A   SEQ ID NO-5
61  Y M S N P D D E N T E L I S K N A R K L G L T V I R G T I   SEQ ID NO-6
48  M A T S G Q Q N N - - - - - - - - - - - I G M V V I R G N S   SEQ ID NO-7

81  V V L I C P Q D G M E A I P N P F I Q Q Q D A   SEQ ID NO-1
82  I T V V S P A D G L E Q I A N P F A T Q E E E   SEQ ID NO-5
91  L V S L S S A E G S D V L - - - Y M Q K         SEQ ID NO-6
67  I I M L - - - E A L E R V                       SEQ ID NO-7
```

FIGURE 3

```
 1  M L F Y S F F K S L V G K D V V V E L K N D L S I C G T L H   SEQ ID NO-3
 1  M L F F S F F K T L V D Q E V V V E L K N D I E I K G T L Q   SEQ ID NO-8

31  S V D Q Y L N I K L T D I S V T D P E K Y P H M L S V K N C   SEQ ID NO-3
31  S V D Q F L N L K L D N I S C T D E K K Y P H L G S V R N I   SEQ ID NO-8

61  F I R G S V V R Y V Q L P A D E V D T Q L L Q D A A R K E A   SEQ ID NO-3
61  F I R G S T V R Y V Y L N K N M V D T N L L Q D A T R R E V   SEQ ID NO-8

91  L Q Q K Q                                                     SEQ ID NO-3
91  M T E R K                                                     SEQ ID NO-8
```

SNRNP SM PROTEINS

FIELD OF THE INVENTION

The present invention relates to nucleic acid and amino acid sequences of novel human small nuclear ribonucleoproteins (snRNP) Sm proteins and to the use of these sequences in the diagnosis, study, prevention and treatment of disease.

BACKGROUND OF THE INVENTION

Small nuclear ribonucleoproteins (snRNPs) are complexes with both RNA and protein components located in the nucleus of all eukaryotic cells. They are involved in various cell processes including mRNA splicing, tRNA processing, and rRNA maturation. At least 5 snRNPs have been identified, each with a specific RNA and one or more specific protein components. In addition, there are a group of eight common proteins that bind tightly to, and are shared by all snRNPs. These molecules, known as the Sm proteins, were originally identified as targets of auto-antibodies from systemic lupus erythematosus (SLE) patients (Lerner MR et al (1979) Proc Natl Acad Sci 76:5495–5499).

Raker VA et al (1996, EMBO J 15: 2256–2269) have shown that Sm proteins are necessary for snRNP biogenesis. Cross-reactivity of Sm proteins suggests that they share common epitopes. Sequence information, in a broad range of Sm proteins from several species, revealed conserved amino acid residues and hydrophobicity within two shared motifs (Seraphin B (1995) EMBO J 14: 2089–2098; Hermann H et al (1995) EMBO J 14: 2076–2088). Sequencing information generated by large-scale sequencing projects in Caenorhabditis elegans and Saccharomyces cerevisiae have revealed additional Sm homologs (Wilson R et al (1994) Nature 368: 32–38; Mallet L et al, unpublished; Van Dyck L et al (1994) Yeast 10: 1663–1673).

Sm Proteins and Disease

SLE is a systemic autoimmune disorder producing a chronic inflammatory disease affecting all organ systems. SLE is unpredictable and often fatal, with renal involvement being the most prevalent life threatening complication. Tests for extractable nuclear antigens, and in particular Sm proteins, are diagnostic for SLE. Anti-Sm antibodies are highly specific to SLE and may also have an important role in the pathogenesis of the disease (Tomer Y et al (1993) Int Arch Allergy Immunol 100: 293–306).

Molecules that are antigenically related to the myelin basic protein are being used in the treatment of multiple sclerosis, another autoimmune disorder (Grgacic E et al (1990) Int Immunol 2: 713–718). It is believed that the immune response can be suppressed by protein fragments which are antigenically related to the target of immune system attack (Teitelbaum D et al (1996) J Neuroimmunol 64: 209–217).

The discovery of additional snRNP Sm genes may provide agents which are more effective in SLE diagnosis and treatment than known agents. A new snRNP Sm protein would satisfy a significant need in the art by providing new agents for the diagnosis, prevention, and treatment of SLE.

SUMMARY

The present invention features two human snRNP Sm proteins (hereinafter referred to individually as HSMPA and HSMPB, and collectively as HSMP), characterized as having homology to C. elegans ZK593.7 (GI 1184607) and S. cerevisiae snRNP Sm E (GI 602898), respectively. Accordingly, the invention features substantially purified snRNP Sm proteins, as shown in amino acid sequence of SEQ ID NO:1 and SEQ ID NO:3, and having characteristics of snRNP Sm proteins.

One aspect of the invention features isolated and substantially purified polynucleotides which encode HSMP. In a particular aspect, the polynucleotides are the nucleotide sequences of SEQ ID NO:2 and SEQ ID NO:4. In addition, the invention features polynucleotide sequences that hybridize under stringent conditions to SEQ ID NO:2 or SEQ ID NO:4.

The invention further relates to nucleic acid sequences encoding HSMP, oligonucleotides, peptide nucleic acids (PNA), fragments, portions or antisense molecules thereof, methods for producing HSMP or fragments thereof, and use of the sequences in expression vectors and host cells comprising polynucleotides which encode HSMP. The present invention also relates to antibodies which bind specifically to HSMP and pharmaceutical compositions comprising substantially purified HSMP or fragments thereof, or antagonists of HSMP.

BRIEF DESCRIPTION OF THE FIGURES

FIG. 1 shows the amino acid sequence (SEQ ID NO:1) and nucleic acid sequence (SEQ ID NO:2) of the novel snRNP Sm protein, HSMPA. The alignment was produced using MACDNASIS software (Hitachi Software Engineering Co Ltd, San Bruno Calif.).

FIG. 2 shows the amino acid sequence (SEQ ID NO:3) and nucleic acid sequence (SEQ ID NO:4) of the novel snRNP Sm protein, HSMPB.

FIG. 3 shows the amino acid sequence alignments among HSMPA (SEQ ID NO:1), C. elegans ZK593.7 (GI 1184607; SEQ ID NO:5), S. cerevisiae JTA107 (GI 1078051; SEQ ID NO:6), and human snRNP Sm G (GI 806566; SEQ ID NO:7). The alignment was produced using the multisequence alignment program of DNAStar software (DNAStar Inc, Madison Wis.).

FIG. 4 shows the amino acid sequence alignments between HSMPB (SEQ ID NO:3), and S. cerevisiae snRNP Sm E (GI 602898; SEQ ID NO:8).

DETAILED DESCRIPTION OF THE INVENTION

Definitions

Figure 5:
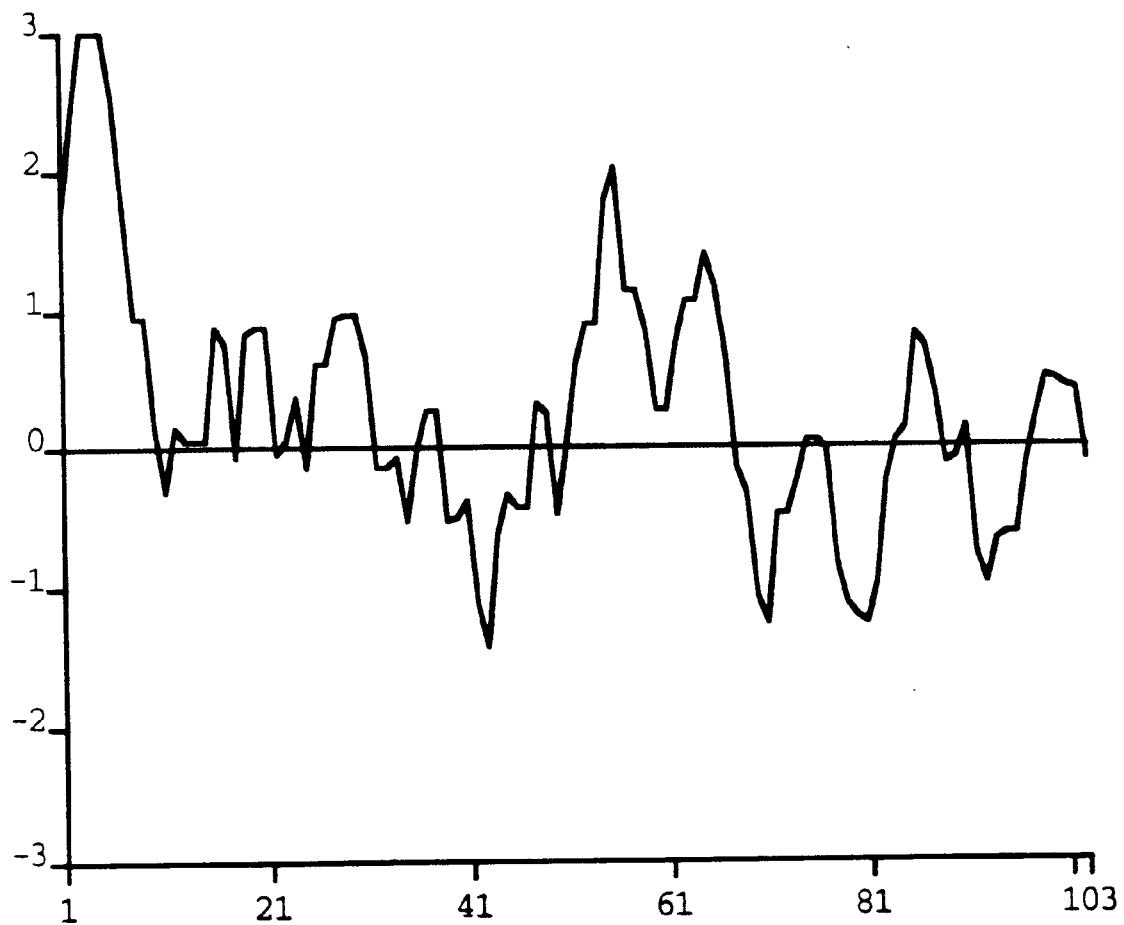
FIG. 5 shows the hydrophobicity plot (generated using MACDNASIS software) for HSMPA, SEQ ID NO:1; the X axis reflects amino acid position, and the negative Y axis, hydrophobicity (FIGS. 5–8).

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to oligopeptide or protein sequence.

"Consensus" as used herein may refer to a nucleic acid sequence 1) which has been resequenced to resolve uncalled bases, 2) which has been extended using XL-PCR (Perkin Elmer, Norwalk Conn.) in the 5' or the 3' direction and resequenced, 3) which has been assembled from the overlapping sequences of more than one Incyte clone GCG Fragment Assembly System, (GCG, Madison Wis.), or 4) which has been both extended and assembled.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen PE et al (1993) Anticancer Drug Des 8:53–63).

As used herein, HSMP refers to the amino acid sequences of substantially purified HSMP obtained from any species, particularly mammalian, including bovine, ovine, porcine, murine, equine, and preferably human, from any source whether natural, synthetic, semi-synthetic or recombinant.

A "variant" of HSMP is defined as an amino acid sequence that is altered by one or more amino acids. The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

A "deletion" is defined as a change in either amino acid or nucleotide sequence in which one or more amino acid or nucleotide residues, respectively, are absent.

An "insertion" or "addition" is that change in an amino acid or nucleotide sequence which has resulted in the addition of one or more amino acid or nucleotide residues, respectively, as compared to the naturally occurring HSMP.

A "substitution" results from the replacement of one or more amino acids or nucleotides by different amino acids or nucleotides, respectively.

The term "biologically active" refers to a HSMP having structural, regulatory or biochemical functions of a naturally occurring HSMP. Likewise, "immunologically active" defines the capability of the natural, recombinant or synthetic HSMP, or any oligopeptide thereof, to induce a specific immune response in appropriate animals or cells and to bind with specific antibodies.

The term "derivative" as used herein refers to the chemical modification of a nucleic acid encoding HSMP or the encoded HSMP. Illustrative of such modifications would be replacement of hydrogen by an alkyl, acyl, or amino group. A nucleic acid derivative would encode a polypeptide which retains essential biological characteristics of natural HSMP.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

"Stringency" typically occurs in a range from about Tm-5° C. (5° C. below the Tm of the probe)to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs J (1994) Dictionary of Biotechnology, Stockton Press, New York N.Y.). Amplification as carried out in the polymerase chain reaction technologies is described in Dieffenbach CW and GS Dveksler (1995, PCR Primer, a Laboratory Manual, Cold Spring Harbor Press, Plainview N.Y.).

Preferred Embodiments

The present invention relates to human snRNP Sm proteins and to the use of the nucleic acid and amino acid sequences in the study, diagnosis, prevention and treatment of disease.

The present invention also encompasses HSMP variants. A preferred HSMP variant is one having at least 80% amino acid sequence similarity to the HSMP amino acid sequence (SEQ ID NO:1 or SEQ ID NO:3), a more preferred HSMP variant is one having at least 90% amino acid sequence similarity to SEQ ID NO:1 or SEQ ID NO:3, and a most preferred HSMP variant is one having at least 95% amino acid sequence similarity to SEQ ID NO:1 or SEQ ID NO:3.

Nucleic acids encoding the human snRNP Sm protein HSMPA of the present invention were first identified in cDNA, Incyte Clone 78585, from a cDNA library made from a synovial membrane tissue from a rheumatoid arthritis patient, SYNORAB01, through a computer-generated search for amino acid sequence alignments. The following Incyte clones (and cDNA libraries from which they were derived) were extended and assembled to create the consensus sequence (SEQ ID NO:2): 8585 (SYNORAB01); 70047 (HUVESTB01); 150123 (FIBRANT01); 358492 (SYNORAB01); 401242 (TMLR3DT01); 612210 (COLNNOT01); 619536 (PGANNOT01); 639204 (BRSTNOT03); 693942 (SYNOPAT03); 766764 (LUNGNOT04); 888397 (STOMTUT01); 960192 (BRSTTUT03); 931234 (CERVNOT01); 1257575 (MENITUT03); 1213909 (BRSTTUT01); 1290549 (BRAINOT11); 1320724 (BLADNOT04); 1491794 (UCMCL5T01); 1613691 (COLNTUT06); 1643806 (HEARFET01); 614167, 1223350 (COLNTUT02); 1309851 (COLNFET02); 1338464 (COLNTUT03); 1375512 (LUNGNOT10); 1461026, 1461048 (PANCNOT04); 1522470, 1522564, 1522649 (BLADTUT04); 1603914 (LUNGNOT15); 1705988 (DUODNOT02); 1737609 (COLNNOT22); and 1805752 (SINTNOT13). HSMPA, SEQ ID NO:1, is encoded by the nucleic acid sequence of SEQ ID NO:2.

HSMPB was first identified in cDNA, Incyte clone 262267 from a cDNA library made from the hNT2 cell line derived from a human teratocarcinoma, HNT2AGT01. The following Incyte clones (and cDNA libraries from which they were derived) were extended and assembled to create the consensus sequence (SEQ ID NO:4): 262267 (HNT2AGT01); 634 (U937NOT01); 629736 (KIDNNOT05); 763210 (BRAITUT02). HSMPB, SEQ ID NO:3, is encoded by the nucleic acid sequence of SEQ ID NO:4.

Figure 6:
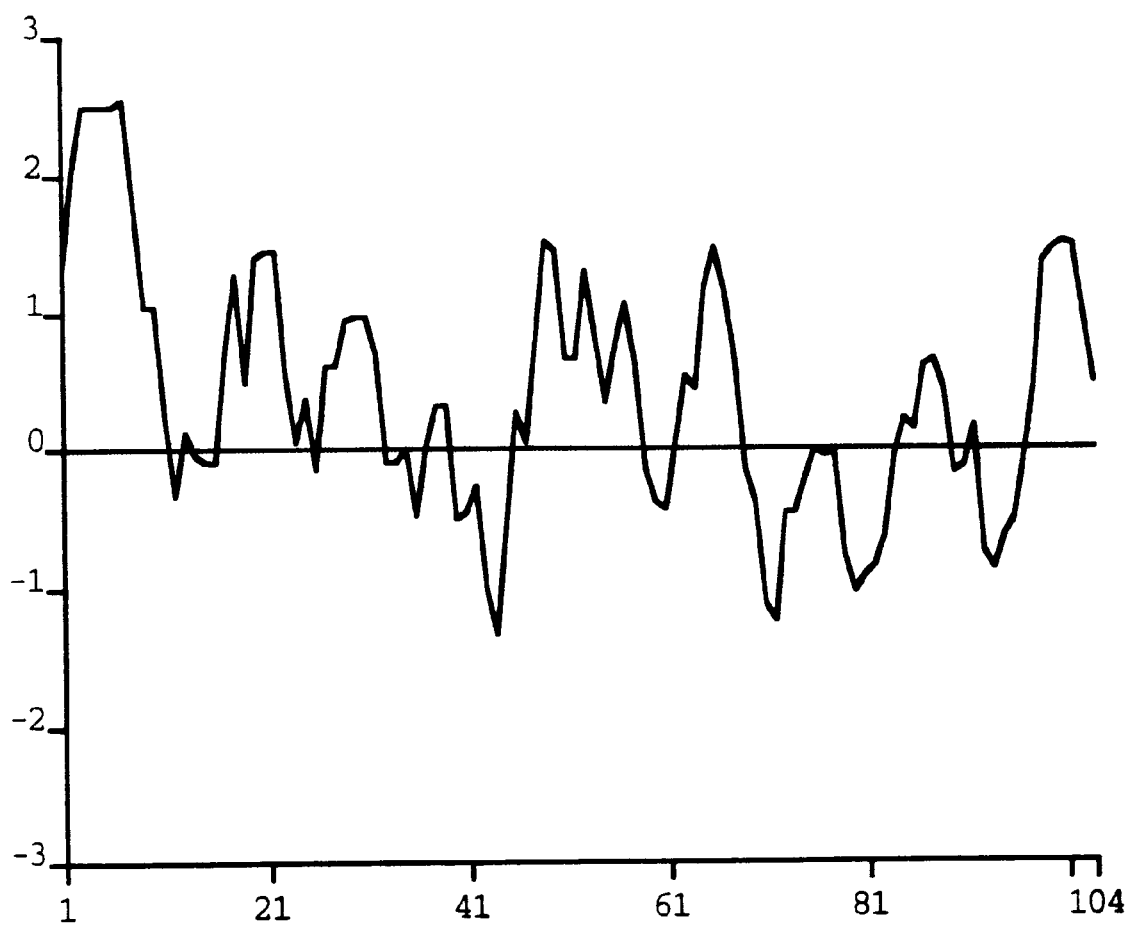
FIG. 6 shows the hydrophobicity plot for C. elegans ZK593.7, SEQ ID NO:5.

The present invention is based, in part, on the chemical and structural homology among HSMPA, C. elegans ZK593.7 (GI 1184607; Wilson et al, supra), S. cerevisiae JTA107 (GI 1078051; Mallet L et al, supra), and human snRNP Sm G (GI 806566; Hermann et al, supra; FIG. 3). HSMPA contains each of the core consensus Sm motif 1 amino acid residues: $G_{30}$, $G_{35}$, $F_{40}$, $D_{41}$, $N_{45}$, $L_{46}$, $L_{48}$, and $E_{53}$ and the Sm motif 2 residues: $L_{71}$, $G_{72}$, $R_{77}$, $G_{78}$, as described by Hermann et al (supra). The novel HSMPA is 103 amino acids long and shares 56% identity with C. elegans ZK593.7. As illustrated by FIGS. 5 and 6, HSMPA and C. elegans ZK593.7 have similar hydrophobicity plots suggesting similar structure.

The present invention is also based, in part, on the chemical and structural homology between HSMPB and S.

Figure 7:
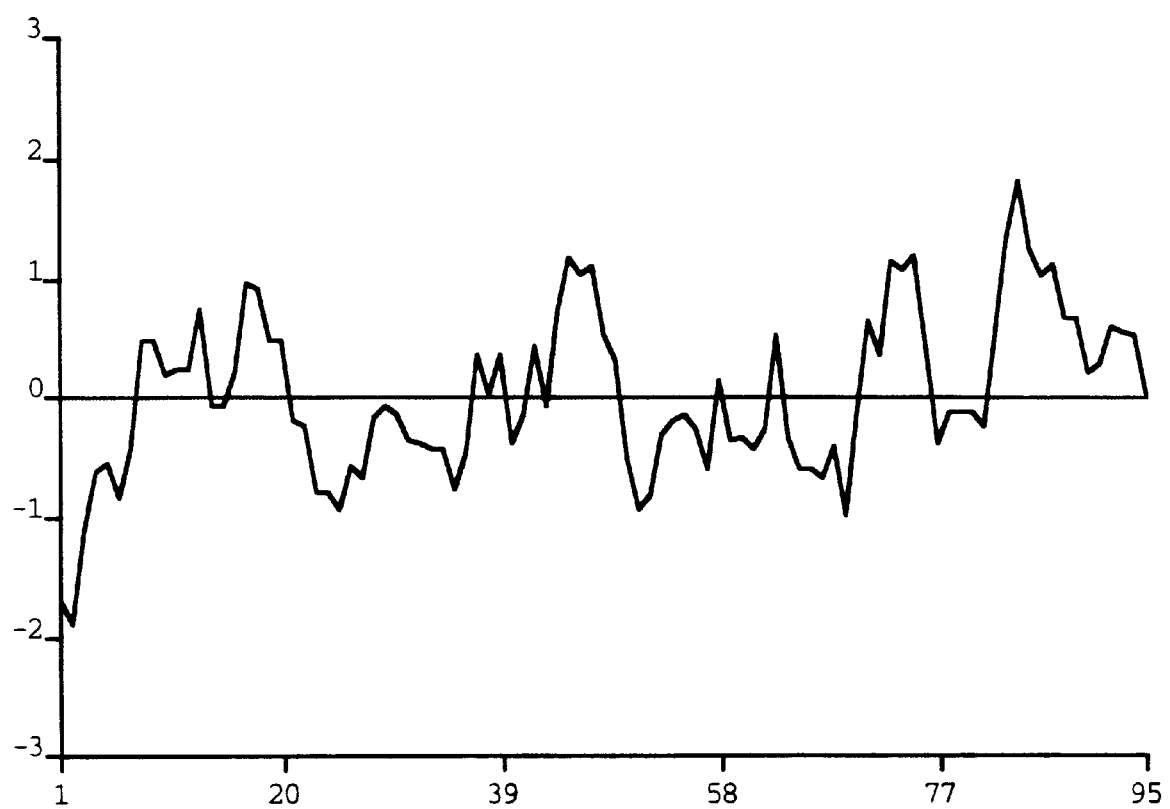
FIG. 7 shows the hydrophobicity plot for HSMPB, SEQ ID NO:3.
Figure 8:
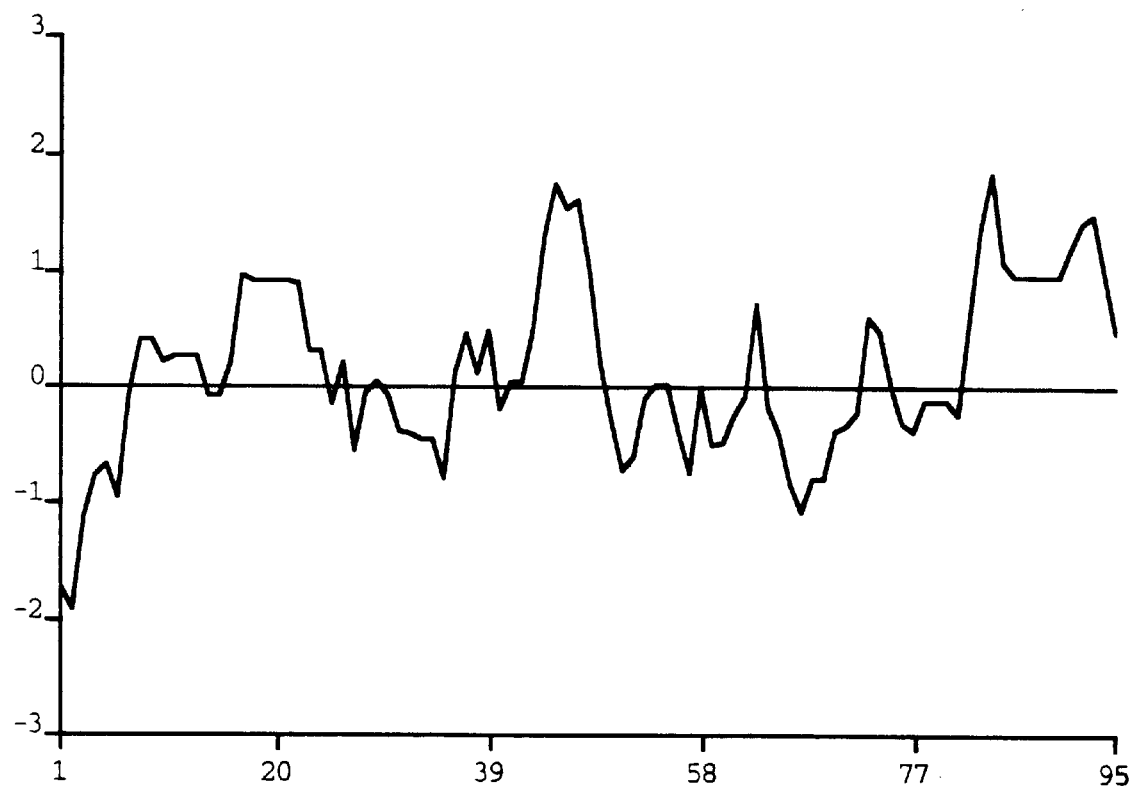
FIG. 8 shows the hydrophobicity plot for S. cerevisiae snRNP Sm E, SEQ ID NO:8.

*cerevisiae* snRNP Sm E (GI 602898; Van Dyck et al, supra) FIG. 4). The novel HSMPB is 95 amino acids long and shares 63% identity with *S. cerevisiae* snRNP Sm E, including Sm core consensus motif amino acid residues $V_{15}$, $G_{27}$, $D_{33}$, $N_{31}$, $L_{40}$, $I_{62}$, $R_{63}$, and $G_{64}$. HSMPB and *S. cerevisiae* snRNP Sm E have similar hydrophobicity plots suggesting similar structure (FIGS. 7 and 8).

The HSMP Coding Sequences

The nucleic acid and deduced amino acid sequences of HSMPA and HSMPB are shown in FIGS. 1 and 2. In accordance with the invention, any nucleic acid sequence which encodes the amino acid sequence of HSMP can be used to generate recombinant molecules which express HSMP. In a specific embodiment described herein, a nucleotide sequence encoding a portion of HSMPA was first isolated as Incyte Clone 78585 from a synovial membrane tissue cDNA library (SYNORAB01). In another specific embodiment described herein, a nucleotide sequence encoding a portion of HSMPB was first isolated as Incyte Clone 262267 from a cDNA library made from hNT2 cell line, (HNT2AGT01).

It will be appreciated by those skilled in the art that as a result of the degeneracy of the genetic code, a multitude of HSMP-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence of naturally occurring HSMP, and all such variations are to be considered as being specifically disclosed.

Although nucleotide sequences which encode HSMP and its variants are preferably capable of hybridizing to the nucleotide sequence of the naturally occurring HSMP under appropriately selected conditions of stringency, it may be advantageous to produce nucleotide sequences encoding HSMP or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HSMP and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding a HSMP and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a sequence encoding HSMP or any portion thereof.

Also included within the scope of the present invention are polynucleotide sequences that are capable of hybridizing to the nucleotide sequence of FIGS. 1 and 2 under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and may be used at a defined stringency.

Altered nucleic acid sequences encoding HSMP which may be used in accordance with the invention include deletions, insertions or substitutions of different nucleotides resulting in a polynucleotide that encodes the same or a functionally equivalent HSMP. The protein may also show deletions, insertions or substitutions of amino acid residues which produce a silent change and result in a functionally equivalent HSMP. Deliberate amino acid substitutions may be made on the basis of similarity in polarity, charge, solubility, hydrophobicity, hydrophilicity, and/or the amphipathic nature of the residues as long as the biological activity of HSMP is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of HSMP. As used herein, an "allele" or "allelic sequence" is an alternative form of HSMP. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, SEQUENASE® (US Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elmer).

Extending the Polynucleotide Sequence

The polynucleotide sequence encoding HSMP may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is that of Parker JD et al (1991; Nucleic Acids Res 19:3055–60). Additionally, one can use PCR, nested primers and PROMOTERFINDER™ libraries to walk in genomic DNA (PROMOTERFINDER™ Clontech (Palo Alto Calif.). This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze the size or confirm the nucleotide sequence of sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. GENOTYPER™ and SEQUENCE NAVIGATOR™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez MC et al (1993) Anal Chem 65:2851–2858).

Expression of the Nucleotide Sequence

In accordance with the present invention, polynucleotide sequences which encode HSMP, fragments of the polypeptide, fusion proteins or functional equivalents thereof may be used in recombinant DNA molecules that direct the expression of HSMP in appropriate host cells. Due to the inherent degeneracy of the genetic code, other DNA sequences which encode substantially the same or a functionally equivalent amino acid sequence, may be used to clone and express HSMP. As will be understood by those of skill in the art, it may be advantageous to produce HSMP-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of HSMP expression or to produce recombinant RNA transcripts having desirable properties, such as a longer half-life, than transcripts produced from naturally occurring sequence.

The nucleotide sequences of the present invention can be engineered in order to alter a HSMP coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant polynucleotides encoding HSMP may be ligated to a heterologous sequence to encode a fusion protein. For example, screening of peptide libraries for inhibitors of HSMP activity, it may be useful to encode a chimeric HSMP protein that is recognized by a commercially available antibody. A fusion protein may also be engineered to contain a cleavage site located between a HSMP sequence and the heterologous protein sequence, so that the HSMP may be cleaved and purified away from the heterologous moiety.

In an alternate embodiment of the invention, the coding sequence of HSMP may be synthesized, whole or in part, using chemical methods well known in the art (see Caruthers MH et al (1980) Nuc Acids Res Symp Ser 215–23, Horn T et al(1980) Nuc Acids Res Symp Ser 225–32, etc). Alternatively, the protein itself could be produced using chemical methods to synthesize a HSMP amino acid sequence, whole or in part. For example, peptide synthesis can be performed using various solid-phase techniques (Roberge JY et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially by preparative high performance liquid chromatography (eg, Creighton (1983) *Proteins, Structures and Molecular Principles*, WH Freeman and Co, New York N.Y.). The composition of the synthetic peptides may be confirmed by amino acid analysis or sequencing (eg, the Edman degradation procedure; Creighton, supra). Additionally the amino acid sequence of HSMP, or any part thereof, may be altered during direct synthesis and/or combined using chemical methods with sequences from other proteins, or any part thereof, to produce a variant polypeptide.

Expression Systems

In order to express a biologically active HSMP, the nucleotide sequence encoding HSMP or its functional equivalent, is inserted into an appropriate expression vector, ie, a vector which contains the necessary elements for the transcription and translation of the inserted coding sequence.

Methods which are well known to those skilled in the art can be used to construct expression vectors containing a HSMP coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual*, Cold Spring Harbor Press, Plainview N.Y. and Ausubel FM et al (1989) *Current Protocols in Molecular Biology*, John Wiley & Sons, New York N.Y.

A variety of expression vector/host systems may be utilized to contain and express a HSMP coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV)

or transfected with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' and 5' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene, LaJolla Calif.) or pSPORT1™ (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of HSMP, vectors based on SV40 or EBV may be used with an appropriate selectable marker.

In bacterial systems, a number of expression vectors may be selected depending upon the use intended for HSMP. For example, when large quantities of HSMP are needed for the induction of antibodies, vectors which direct high level expression of fusion proteins that are readily purified may be desirable. Such vectors include, but are not limited to, the multifunctional $E.$ $coli$ cloning and expression vectors such as BLUESCRIPT® (Stratagene), in which the HSMP coding sequence may be ligated into the vector in frame with sequences for the amino-terminal Met and the subsequent 7 residues of $\beta$-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, $S.$ $cerevisiae$, a number of vectors containing constitutive or inducible promoters such as alpha factor, alcohol oxidase and PGH may be used. For reviews, see Ausubel et al (supra) and Grant et al (1987) $Methods$ $in$ $Enzymology$ 153:516–544.

In cases where plant expression vectors are used, the expression of a sequence encoding HSMP may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi RM (1991) Results Probl Cell Differ 17:85–105) may be used. These constructs can be introduced into plant cells by direct DNA or pathogen-mediated transfection. For reviews of such techniques, see Hobbs S or Murry LE in McGraw Hill $Yearbook$ $of$ $Science$ $and$ $Technology$ (1992) McGraw Hill New York N.Y., pp 191–196 or Weissbach and Weissbach (1988) $Methods$ $for$ $Plant$ $Molecular$ $Biology$, Academic Press, New York N.Y., pp 421–463.

An alternative expression system which could be used to express HSMP is an insect system. In one such system, $Autographa$ $californica$ nuclear polyhedrosis virus (AcNPV) is used as a vector to express foreign genes in $Spodoptera$ $frugiperda$ cells or in Trichoplusia larvae. The HSMP coding sequence may be cloned into a nonessential region of the virus, such as the polyhedrin gene, and placed under control of the polyhedrin promoter. Successful insertion of HSMP will render the polyhedrin gene inactive and produce recombinant virus lacking coat protein. The recombinant viruses are then used to infect $S.$ $frugiperda$ cells or Trichoplusia larvae in which HSMP is expressed (Smith et al (1983) J Virol 46:584; Engelhard EK et al (1994) Proc Nat Acad Sci 91:3224–7).

In mammalian host cells, a number of viral-based expression systems may be utilized. In cases where an adenovirus is used as an expression vector, a HSMP coding sequence may be ligated into an adenovirus transcription/translation complex consisting of the late promoter and tripartite leader sequence. Insertion in a nonessential E1 or E3 region of the viral genome will result in a viable virus capable of expressing HSMP in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a HSMP sequence. These signals include the ATG initiation codon and adjacent sequences. In cases where HSMP, its initiation codon and upstream sequences are inserted into the appropriate expression vector, no additional translational control signals may be needed. However, in cases where only coding sequence, or a portion thereof, is inserted, exogenous transcriptional control signals including the ATG initiation and termination codons should be provided. Furthermore, the initiation codon must be in the correct reading frame to ensure translation of the entire insert. Exogenous translational elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, HEK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express HSMP may be transfected using expression vectors which contain endogenous expression elements and may also contain viral origins of replication and a selectable marker gene on the same or separate vectors. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transfected cells can be proliferated using tissue culture techniques appropriate to the cell type.

Any number of selection systems may be used to recover transfected cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman SC and RC Mulligan (1988) Proc Natl Acad Sci 85:8047–51). Recently, the use of visible markers has gained popularity with such markers as anthocyanins, $\beta$ glucuronidase and its substrate, GUS, and luciferase and its substrate, luciferin, being widely used not only to identify transfectants, but also to quantify the amount of transient or stable protein expression attributable to a specific vector system (Rhodes CA et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the HSMP is inserted within a marker gene sequence, recombinant cells containing HSMP can be identified by the absence of marker gene function. Alternatively, a marker gene can be placed in tandem with a HSMP sequence under the control of a single promoter. Expression of the marker gene in response to induction or selection usually indicates expression of the tandem HSMP as well.

Alternatively, host cells which contain the coding sequence for HSMP and express HSMP may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding HSMP can be detected by DNA-DNA or DNA-RNA hybridization or amplification using probes, portions or fragments of polynucleotides encoding HSMP. Nucleic acid amplification based assays involve the use of oligonucleotides or oligomers based on the HSMP-encoding sequence to detect transformants containing DNA or RNA encoding HSMP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of HSMP, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HSMP is preferred, but a competitive binding assay may be employed. These and other assays are described, among other places, in Hampton R et al (1990, Serological Methods, a Laboratory Manual, APS Press, St Paul Mich.) and Maddox Del. et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to polynucleotides encoding HSMP include oligolabeling, nick translation, end-labeling or PCR amplification using a labeled nucleotide. Alternatively, the sequence encoding HSMP, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of HSMP

Host cells transformed with a nucleotide sequence encoding HSMP may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing polynucleotides encoding HSMP can be designed with signal sequences which direct secretion of HSMP through a prokaryotic or eukaryotic cell membrane. Other recombinant constructions may join HSMP to nucleotide sequence encoding a polypeptide domain which will facilitate purification of soluble proteins (Kroll DJ et al (1993) DNA Cell Biol 12:441–53; of discussion of vectors infra containing fusion proteins).

Purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and HSMP is useful to facilitate purification. One such expression vector provides for expression of a fusion protein compromising a HSMP and contains nucleic acid encoding 6 histidine residues followed by thioredoxin and an enterokinase cleavage site. The histidine residues facilitate purification on IMIAC (immobilized metal ion affinity chromatography as described in Porath et al (1992) Protein Expression and Purification 3: 263–281) while the enterokinase cleavage site provides a means for purifying HSMP from the fusion protein.

In addition to recombinant production, fragments of HSMP may be produced by direct peptide synthesis using solid-phase techniques (of Stewart et al (1969) *Solid-Phase Peptide Synthesis*, WH Freeman Co, San Francisco; (Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of HSMP may be chemically synthesized separately and combined using chemical methods to produce the full length molecule.

Therapeutic Uses of HSMP

The rationale for use of the polypeptide sequences disclosed herein is based in part on the chemical and structural homology among HSMPA, *C. elegans* ZK593.7 (GI 1184607; Wilson et al, supra), *S. cerevisiae* JTA107 (GI 1078051; Mallet L et al, supra), and human snRNP Sm G (GI 806566; Hermann et al, supra) and between HSMPB and *S. cerevisiae* snRNP Sm E (GI 602898; Van Dyck et al, supra).

The presence of anti-Sm antibodies in the serum of a subject is diagnostic for SLE. These autoantibodies may have a role in SLE pathogenesis. Their antigenic properties make Sm proteins potential agents for the development of SLE diagnostics and therapeutics. The snRNP Sm protein HSMP or an HSMP derivative, may be used to diagnose, prevent, or treat SLE.

Using methods known in the art HMSP-specific agonists or antagonists may be developed. These may be used to specifically modulate the activity of HMSP and would be therapeutically useful for decreasing the harmful effects of the anti-Sm immune response in SLE.

HSMP Antibodies

HSMP-specific antibodies are useful for the diagnosis of conditions and diseases associated with expression of HSMP. Such antibodies may include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

HSMP for antibody induction does not require biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of HSMP amino acids may be fused with those of another protein such as keyhole limpet hemocyanin and antibody produced against the chimeric molecule. Procedures well known in the art can be used for the production of antibodies to HSMP.

For the production of antibodies, various hosts including goats, rabbits, rats, mice, etc may be immunized by injection with HSMP or any portion, fragment or oligopeptide which retains immunogenic properties. Depending on the host species, various adjuvants may be used to increase immunological response. Such adjuvants include but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to HSMP may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce HSMP-specific single chain antibodies Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for HSMP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse WD et al (1989) Science 256:1275–1281).

A variety of protocols for competitive binding or immunoradiometric assays using either polyclonal or monoclonal antibodies with established specificities are well known in the art. Such immunoassays typically involve the formation of complexes between HSMP and its specific antibody and the measurement of complex formation. A two-site, monoclonal-based immunoassay utilizing monoclonal antibodies reactive to two noninterfering epitopes on a specific HSMP protein is preferred, but a competitive binding assay may also be employed. These assays are described in Maddox DE et al (1983, J Exp Med 158:1211).

Diagnostic Assays Using HSMP Specific Antibodies

Particular HSMP antibodies are useful for the diagnosis of conditions or diseases characterized by expression of HSMP or in assays to monitor patients being treated with HSMP, agonists or inhibitors. Diagnostic assays for HSMP include methods utilizing the antibody and a label to detect HSMP in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring HSMP, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HSMP is preferred, but a competitive binding assay may be employed. These assays are described, among other places, in Maddox, DE et al (1983, J Exp Med 158:1211).

In order to provide a basis for diagnosis, normal or standard values for HSMP expression must be established. This is accomplished by combining body fluids or cell extracts taken from normal subjects, either animal or human, with antibody to HSMP under conditions suitable for complex formation which are well known in the art. The amount of standard complex formation may be quantified by comparing various artificial membranes containing known quantities of HSMP with both control, and disease samples from biopsied tissues. Then, standard values obtained from normal samples may be compared with values obtained from samples from subjects potentially affected by disease. Deviation between standard and subject values establishes the presence of disease state.

Drug Screening

HSMP, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between HSMP and the agent being tested, may be measured.

Another technique for drug screening which may be used provides for high throughput screening of compounds having suitable binding affinity to the HSMP is described in detail in "Determination of Amino Acid Sequence Antigenicity" by Geysen HM, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of HSMP and washed. Bound HSMP is then detected by methods well known in the art. Purified HSMP can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding HSMP specifically compete with a test compound for binding HSMP. In this manner, the antibodies can be used to detect the presence of any peptide which shares one or more antigenic determinants with HSMP.

Diagnostic and Therapeutic Uses of the Polynucleotide

A polynucleotide encoding HSMP, or any part thereof, may be used for diagnostic and/or therapeutic purposes. For diagnostic purposes, polynucleotides encoding HSMP of this invention may be used to detect and quantitate gene expression in biopsied tissues in which expression of HSMP may be implicated. The diagnostic assay is useful to distinguish between absence, presence, and excess expression of HSMP and to monitor regulation of HSMP levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding HSMP or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring sequences encoding HSMP, alleles or related sequences.

Probes may also be used for the detection of related sequences and should preferably contain at least 50% of the nucleotides from any of these HSMP encoding sequences. The hybridization probes of the subject invention may be derived from the nucleotide sequence of SEQ ID NO:2, SEQ ID NO:4, or from genomic sequence including promoter, enhancer elements and introns of the naturally occurring HSMP. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for DNAs encoding HSMP include the cloning of nucleic acid sequences encoding HSMP or HSMP derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Polynucleotide sequences encoding HSMP may be used for the diagnosis of conditions or diseases with which the expression of HSMP is associated. For example, polynucleotide sequences encoding HSMP may be used in hybridization or PCR assays of fluids or tissues from biopsies to detect HSMP expression. The form of such qualitative or quantitative methods may include Southern or northern analysis, dot blot or other membrane-based technologies; PCR technologies; dip stick, pIN, chip and ELISA technologies. All of these techniques are well known in the art and are the basis of many commercially available diagnostic kits.

The nucleotide sequences encoding HSMP disclosed herein provide the basis for assays that detect activation or induction associated with SLE. The nucleotide sequence encoding HSMP may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding HESMP in the sample indicates the presence of the associated disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for HSMP expression must be established. This is accomplished by combining body fluids or cell extracts taken from normal subjects, either animal or human, with HSMP, or a portion thereof, under conditions suitable for hybridization or amplification. Standard hybridization may be quantified by comparing the values obtained for normal subjects with a dilution series of HSMP run in the same experiment where a known amount of a substantially purified HSMP is used. Standard values obtained from normal samples may be compared with values obtained from samples from patients afflicted with HSMP-associated diseases. Deviation between standard and subject values is used to establish the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR may be used to detect or quantitate the expression of HSMP. PCR primers are generally chemically synthesized, but they may be generated enzymatically or produced from a recombinant source. Oligomers generally comprise two nucleotide sequences, one with sense orientation (5'->3') and one with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby PC et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or calorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Based upon its homology to gene encoding snRNP Sm proteins polynucleotide sequences encoding HSMP disclosed herein may be useful in the treatment of SLE.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense polynucleotides of the gene encoding HSMP. See, for example, the techniques described in Sambrook et al (supra) and Ausubel et al (supra).

The polynucleotides comprising full length cDNA sequence and/or its regulatory elements enable researchers to use sequences encoding HSMP as an investigative tool in sense (Youssoufian H and HF Lodish 1993 Mol Cell Biol 13:98–104) or antisense (Eguchi et al (1991) Annu Rev Biochem 60:631-652) regulation of gene function. Such technology is now well known in the art, and sense or antisense oligomers, or larger fragments, can be designed from various locations along the coding or control regions.

Genes encoding HSMP can be turned off by transfecting a cell or tissue with expression vectors which express high levels of a desired HSMP-encoding fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of gene encoding HSMP, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee JE et al (In: Huber BE and BI Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of sequences encoding HSMP.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HSMP. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference. Delivery by transfection and by liposome are quite well known in the art.

Furthermore, the nucleotide sequences for HSMP disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for HSMP can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price CM (1993; Blood Rev 7:127–34) and Trask BJ (1991; Trends Genet 7:149–54).

The technique of fluorescent in situ hybridization of chromosome spreads has been described, among other places, in Verma et al (1988) *Human Chromosomes: A Manual of Basic Techniques*, Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of the gene encoding HSMP on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers may be used for extending genetic maps. For example, a sequence tagged site based map of the human genome was recently published by the Whitehead-MIT Center for Genomic Research (Hudson TJ et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of HSMP, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

It is contemplated, for example, that HSMP or a HSMP derivative can be delivered in a suitable formulation to stop the progression of SLE.

The examples below are provided to illustrate the subject invention and are not included for the purpose of limiting the invention.

EXAMPLES

I cDNA Library Construction

SYNORAB01 library

The sequence was identified among the cDNAs (Incyte Clone 78585) comprising the rheumatoid synovium library (SYNORAB01). The synovial joint tissue was obtained from a 68 yr old Caucasian male with rheumatoid arthritis undergoing hip replacement surgery. The frozen tissue was ground in a mortar and pestle and lysed immediately in buffer containing guanidinium isothiocyanate. Lysis was followed by several phenol-chloroform extractions and ethanol precipitations. Poly-A$^+$ mRNA was isolated using biotinylated oligo d(T) and streptavidin coupled to paramagnetic particles (Poly(A) Tract Isolation System, Promega, Madison Wis.). Using this poly-A$^+$ mRNA, a custom cDNA library was constructed by Stratagene (La Jolla Calif.).

The phagemid forms of individual cDNA clones were obtained by the in vivo excision process, in which XL1-BLUE™ cells were coinfected with an f1 helper phage. Proteins derived from both the lambda and f1 helper phages initiated new DNA synthesis from defined sequences on the lambda DNA to create a smaller, single-stranded circular phagemid molecule that includes all the DNA sequence of the pBluescript™ plasmid (Stratagene) and the cDNA insert. The phagemid DNA was released from the cells, purified, and used to reinfect fresh SOLR™ cells (Stratagene), which produced the double-stranded phagemid. Because the phagemid carries the gene for β-lactamase, the newly transformed bacteria were selected on medium containing ampicillin. Phagemid DNA was purified using the QIAWELL-8® Plasmid Purification System (QIAGEN Inc., Chatworth Calif.).

HNT2AGT1 library

The hNT2 cell line exhibits characteristics of a committed neuronal precursor cell which is at an early stage of development. The hNT2 cell line can be induced by retinoic acid (RA) to differentiate, as described in Andrews PW (1984) Dev Biol 103:285–293.

For purposes of this invention, hNT2 cells were induced with RA. The method used in the present invention involved suspending hNT2 cells in Dulbecco's modified Eagle's medium (DMEM) including 10% fetal bovine serum and penicillin/streptomycin, treating the cells with 10 mM RA twice a week for 5 weeks. The cells were differentially harvested and replated, and exposed to mitotic inhibitors (1 mM cytosine arabinose, 10 mM fluorodeoxyuridine, and 10 mM uridine) for two weeks. The neurons were again differentially harvested, replated and allowed to mature further for 4 weeks in 50% hNT Neuron Conditioned Medium including DMEM and 10% fetal bovine serum. This procedure created cells similar to those of the postmitotic neuronal cell line of Lee and Pleasure (hNT2-N cell line) and were named HNT2AGT1 cells.

The HNT2AGT1 library was constructed essentially as described below. Stratagene isolated the mRNA. First strand cDNA synthesis was accomplished using an oligo d(T) primer/linker which also contained an XhoI restriction site. Second strand synthesis was performed using a combination of DNA polymerase I, *E. coli* ligase and RNase H, followed by the addition of an EcoRI adaptor to the blunt ended cDNA. The EcoRI adapted, double-stranded cDNA was then digested with XhoI restriction enzyme and fractionated to obtain sequences which exceeded 800 bp in size. The cDNAs were inserted into the LambdaZap vector system (Stratagene); then the vector which contains the pBluescript$^a$ phagemid (Stratagene) was transformed into *E. coli* host cells strain XL1-BlueMRF$^a$ (Stratagene).

The phagemid forms of individual cDNA clones were obtained by the in vivo excision process. Enzymes from both pBluescript and a cotransformed f1 helper phage nicked the DNA, initiated new DNA synthesis, and created the smaller, single-stranded circular phagemid molecules which contained the cDNA insert. The phagemid DNA was released, purified, and used to reinfect fresh host cells (SOLR, Stratagene). Presence of the phagemid which carries the gene for β-lactamase allowed transformed bacteria to grow on medium containing ampicillin.

II Sequencing of cDNA Clones

The cDNA inserts from random isolates of the library was sequenced by the method of Sanger F and AR Coulson (1975; J Mol Biol 94:441f). Methods for DNA sequencing are well known in the art. Conventional enzymatic methods employed DNA polymerase Klenow fragment, SEQUENASE® (US Biochemical Corp, Cleveland, Ohio) or Taq polymerase to extend DNA chains from an oligonucleotide primer annealed to the DNA template of interest. Methods have been developed for the use of both single- and double-stranded templates. The chain termination reaction products were electrophoresed on urea-acrylamide gels and detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day (using machines such as the Catalyst 800 or a Hamilton Micro Lab 2200 (Hamilton, Reno Nev.) in combination with four Peltier Thermal Cyclers (PTC200 from MJ Research, Watertown Mass.) and the Applied Biosystems 377 or 373 DNA sequencers).

III Homology Searching of cDNA Clones and Their Deduced Proteins

Each cDNA was compared to sequences in GenBank using a search algorithm developed by Applied Biosystems and incorporated into the INHERIT™ 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT- 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul SF (1993) J Mol Evol 36:290–300; Altschul, SF et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPS) within the context of the entire database search. Any database sequence whose match satisfies E is reported in the program output.

IV Northern Analysis

Northern analysis is a laboratory technique used to detect the presence of a transcript of a gene and involves the hybridization of a labelled nucleotide sequence to a membrane on which RNAs from a particular cell type or tissue have been bound (Sambrook et al. supra).

Analogous computer techniques using BLAST (Altschul SF 1993 and 1990, supra) are used to search for identical or related molecules in nucleotide databases such as GenBank or the LIFESEQ™ database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into acccount both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of the search are reported as a list of 1) libraries in which the full length sequence, or parts thereof, is represented 2) the abundance of the sequence, and 3) the percent abundance. Abundance directly reflects the number of times a particular transcript is present in a cDNA library, and percent abundance is abundance divided by the total number of sequences examined in the library.

V Extension of HSMP-Encoding Polynucleotides to Full Length or to Recover Regulatory Elements Full length HSMP-encoding nucleic acid sequences (SEQ ID NO:2 or SEQ ID NO:4) are used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known HSMP-encoding sequence "outward" generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 or SEQ ID NO:4 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [γ-$^{32}$P] adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco PI, Pst I, Xba 1, or Pvu II; DuPont NEN®)

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VII Antisense Molecules

The HSMP-encoding sequence, or any part thereof, is used to inhibit in vivo or in vitro expression of naturally occurring HSMP. Although use of antisense oligonucleotides, comprising about 20 base-pairs, is specifically described, essentially the same procedure is used with larger cDNA fragments. An oligonucleotide based on the coding sequence of HSMP, as shown in FIGS. 1 and 2, is used to inhibit expression of naturally occurring HSMP. The complementary oligonucleotide is designed from the most unique 5' sequence as shown in FIGS. 1 and 2, and used either to inhibit transcription by preventing promoter binding to the upstream nontranslated sequence or translation of a HSMP-encoding transcript by preventing the ribosome from binding. Using an appropriate portion of the leader and 5' sequence of SEQ ID NO:2 or SEQ ID NO:4, an effective antisense oligonucleotide includes any 15–20 nucleotides spanning the region which translates into the signal or early coding sequence of the polypeptide as shown in FIGS. 1 and 2.

VIII Expression of HSMP

Expression of the HSMP is accomplished by subcloning the cDNAs into appropriate vectors and transfecting the vectors into host cells. In this case, the cloning vector, pSport, previously used for the generation of the cDNA library is used to express HSMP in E. coli. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first seven residues of β-galactosidase, about 5 to 15 residues of linker, and the full length HSMP-encoding sequence. The signal sequence directs the secretion of HSMP into the bacterial growth media which can be used directly in the following assay for activity.

IX HSMP Activity

HSMP's association with RNA component of snRNPs can be measured by an assay described by Seraphin (supra). Sequences derived from the *Staphylococcus aureus* protein A coding for two IgG binding sites are fused in-frame downstream of sequences coding for HSMP. A control plasmid lacking HSMP sequences is also made. The plasmids are introduced into yeast cells, selected for, and then total cell extracts are produced. Protein A-containing complexes present in these extracts are immunoprecipitated using IgGs coupled to agarose beads. The presence of specific RNAs in the pellet is quantitatively assayed by primer extension using primers specific for the RNA component of snRNPs.

X Production of HSMP Specific Antibodies

HSMP substantially purified using PAGE electrophoresis (Sambrook, supra) is used to immunize rabbits and to produce antibodies using standard protocols. The amino acid sequence translated from HSMP is analyzed using DNAStar software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIGS. 5 and 7) is described by Ausubel FM et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel FM et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HSMP Using Specific Antibodies

Naturally occurring or recombinant HSMP is substantially purified by immunoaffinity chromatography using antibodies specific for HSMP. An immunoaffinity column is constructed by covalently coupling HSMP antibody to an activated chromatographic resin such as CnBr-activated Sepharose (Pharmacia Biotech). After the coupling, the resin is blocked and washed according to the manufacturer's instructions.

Media containing HSMP is passed over the immunoaffinity column, and the column is washed under conditions that allow the preferential absorbance of HSMP (eg, high ionic strength buffers in the presence of detergent). The column is eluted under conditions that disrupt antibody/HSMP binding (eg, a buffer of pH 2–3 or a high concentration of a chaotrope such as urea or thiocyanate ion), and HSMP is collected.

XII Identification of Molecules Which Interact with HSMP

HSMP, or biologically active fragments thereof, are labelled with $^{125}$I Bolton-Hunter reagent (Bolton, AE and Hunter, WM (1973) Biochem J 133: 529). Candidate molecules previously arrayed in the wells of a 96 well plate are incubated with the labelled HSMP, washed and any wells with labelled HSMP complex are assayed. Data obtained using different concentrations of HSMP are used to calculate values for the number, affinity, and association of HSMP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. An isolated and purified polynucleotide encoding a polypeptide comprising the amino acid sequence of SEQ ID NO:1.

2. The isolated and purified polynucleotide of claim 1 consisting of SEQ ID NO:2.

3. A polynucleotide which is complementary to SEQ ID NO:2.

4. An expression vector containing the polynucleotide of claim 1.

5. A host cell containing the vector of claim 4.

6. A method for producing a polypeptide comprising the amino acid sequence of SEQ ID NO:1, the method comprising the steps of:

a) culturing the host cell of claim 6 under conditions suitable for the expression of the polypeptide; and b) recovering the polypeptide from the host cell culture.

7. An isolated and purified polynucleotide encoding a polypeptide comprising the amino acid sequence of SEQ ID NO:3.

8. The isolated and purified polynucleotide of claim 7 consisting of SEQ ID NO:4.

9. A polynucleotide which is complementary to SEQ ID NO:4.

10. An expression vector containing the polynucleotide of claim 7.

11. A host cell containing the vector of claim 10.

12. A method for producing a polypeptide comprising the amino acid sequence of SEQ ID NO:3, the method comprising the steps of:
 a) culturing the host cell of claim 11 under conditions suitable for the expression of the polypeptide; and
 b) recovering the polypeptide from the host cell culture.

* * * * *

UNITED STATES PATENT AND TRADEMARK OFFICE
CERTIFICATE OF CORRECTION

PATENT NO. : 5,955,299
DATED : September 21, 1999
INVENTOR(S) : Hillman et al.

It is certified that error appears in the above-identified patent and that said Letters Patent is hereby corrected as shown below:

<u>Column 36,</u>
Line 61, replace "claim 6" with -- claim 5 --.

Signed and Sealed this

Seventh Day of August, 2001

*Attest:*

NICHOLAS P. GODICI
*Attesting Officer*  *Acting Director of the United States Patent and Trademark Office*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 103 amino acids
      (B) TYPE: amino acid
      (C) STRANDEDNESS: single
      (D) TOPOLOGY: linear (ii) MOLECULE TYPE: peptide (vii) IMMEDIATE SOURCE:
      (A) LIBRARY:
      (B) CLONE: Consensus (xi) SEQUENCE DESCRIPTION: SEQ ID NO:1:

```
Met Ala Asp Lys Glu Lys Lys Lys Glu Ser Ile Leu Asp Leu Ser
 1               5                  10                  15

Lys Tyr Ile Asp Lys Thr Ile Arg Val Lys Phe Gln Gly Arg Glu
                20                  25                  30

Ala Ser Gly Ile Leu Lys Gly Phe Asp Pro Leu Leu Asn Leu Val
                35                  40                  45

Leu Asp Gly Thr Ile Glu Tyr Met Arg Asp Pro Asp Asp Gln Tyr Lys Leu
                50                  55                  60

Thr Glu Asp Thr Arg Gln Leu Gly Leu Val Val Cys Arg Gly Thr Ser
65                  70                  75                  80

Val Val Leu Ile Cys Pro Gln Asp Gly Met Glu Ala Ile Pro Asn Pro
                        85                  90                  95

Phe Ile Gln Gln Gln Asp Ala
                100
```

(2) INFORMATION FOR SEQ ID NO:2:

(i) SEQUENCE CHARACTERISTICS:
      (A) LENGTH: 498 base pairs
      (B) TYPE: nucleic acid
      (C) STRANDEDNESS: single
      (D) TOPOLOGY: linear (ii) MOLECULE TYPE: cDNA (vii) IMMEDIATE SOURCE:
      (A) LIBRARY:
      (B) CLONE: Consensus (xi) SEQUENCE DESCRIPTION: SEQ ID NO:2:

```
CGGCTCGAGG CCACACGGCG CGACAAGATG GCGGATAAGG AGAAGAAGAA AAAGGAGAGC      60

ATCTTGGACT TGTCCAAGTA CATCGACAAG ACGATCCGGG TAAAGTTCCA GGGAGGCCGC     120

GAAGCCAGTG GAATCCTGAA GGGCTTCGAC CCACTCCTCA ACCTTGTGCT GGACGGCACC     180

ATTGAGTACA TGCGAGACCC TGACGACCAG TACAAGCTCA CGGAGGACAC CCGGCAGCTG     240

GGCCTCGTGG TGTGCCGGGG CACGTCCGTG GTGCTAATCT GCCCGCAGGA CGGCATGGAG     300

GCCATCCCCA ACCCCTTCAT CCAGCAGCAG GACGCCTAGC CTGGCCGGGG GCGCGGGGGG     360
```

```
TGCAGGGCAG GCCCGAGCAG CTCGGTTTCC CGCGGACTTG GCTGCTGCTC CCACCGCAGT      420

ACCGCCTCCT GGAACGGAAG CATTTTCCTT TTTGTATAGG TTGAATTTTT GTTTTCTTAA      480

TAAAATTGCA AACCTCAA                                                     498
```

(2) INFORMATION FOR SEQ ID NO:3:

(i) SEQUENCE CHARACTERISTICS:
        (A) LENGTH: 95 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY:
        (B) CLONE: Consensus (xi) SEQUENCE DESCRIPTION: SEQ ID NO:3:

```
Met Leu Phe Tyr Ser Phe Phe Lys Ser Leu Val Gly Lys Asp Val Val
 1               5                  10                  15

Val Glu Leu Lys Asn Asp Leu Ser Ile Cys Gly Thr Leu His Ser Val
            20                  25                  30

Asp Gln Tyr Leu Asn Ile Lys Leu Thr Asp Ile Ser Val Thr Asp Pro
        35                  40                  45

Glu Lys Tyr Pro His Met Leu Ser Val Lys Asn Cys Phe Ile Arg Gly
    50                  55                  60

Ser Val Val Arg Tyr Val Gln Leu Pro Ala Asp Glu Val Asp Thr Gln
65                  70                  75                  80

Leu Leu Gln Asp Ala Ala Arg Lys Glu Ala Leu Gln Gln Lys Gln
                85                  90                  95
```

(2) INFORMATION FOR SEQ ID NO:4:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY:
        (B) CLONE: Consensus (xi) SEQUENCE DESCRIPTION: SEQ ID NO:4:

```
TACTCTACCC AGCTTGCGCT CCCCAGCCGC AAGTNGGCCG CGCTTTGCCC GTCAGCGCTT       60

GGAGCTTTCT GCGTCGCTTC CCGCTGCGCC TGCGCGGTCC CGCCTCGYCC CACGCGCGGG      120

CTCGCGCTTC GGTTTCCCCA GACCTGCTCG CAGCACCCTG CTGTCTTCCC GGTCCGGCCC      180

GCTGCCCGCG GCGCCAGCAC CATGCTCTTC TATTCTTTTT TCAAGTCCCT TGTGGGCAAG      240

GATGTGGTCG TGGAACTAAA GAATGACCTG AGCATCTGTG GAACCCTCCA TTCTGTGGAT      300

CAGTATCTCA ACATCAAACT AACTGACATC AGTGTCACAG ACCCTGAGAA ATACCCTCAC      360

ATGTTATCAG TGAAGAACTG CTTCATTCGG GGCTCAGTGG TCCGATACGT GCAGCTGCCA      420

GCAGATGAGG TCGACACACA GTTGCTACAG GATGCGGCAA GGAAGGAAGC CCTGCAGCAG      480

AAACAGTGAT GGCTCCTTCT CTTTTCCCTC CCTTTCATTG GTGACCCATA ACCCCAAGTC      540

CCAGCCCAGA ACCCCTAACC CCAATACTTT GAAGGGGTTT TGTTTTTTTA CTAATGATGG      600

TTTTGTGGGT TTTTTTTAAG GGATGAGTGG ATGAGAGGAG TAATAGGGAA CAGCTATCCT      660
```

```
CTCTTGAGAA GGGGAGGATA AGTAGGCTGG GAAACTTCAA AGCCTTCCCA GTCCCCAGCA        720
```

(2) INFORMATION FOR SEQ ID NO:5:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 1184607

(xi) SEQUENCE DESCRIPTION: SEQ ID NO:5:

```
Met Ser Lys Asp Glu Gly Lys Arg Lys Lys Glu Ser Val Val Asp Leu
 1               5                  10                  15

Thr Arg Phe Leu Asp Lys Glu Ile Arg Val Lys Phe Gln Gly Gly Arg
             20                  25                  30

Glu Ala Ser Gly Val Leu Arg Gly Phe Asp Gln Leu Leu Asn Met Val
         35                  40                  45

Leu Asp Asp Cys Arg Glu Tyr Leu Arg Asp Pro Gln Asn Pro Ser Val
 50                  55                  60

Val Gly Asp Glu Thr Arg Gln Leu Gly Leu Ile Val Ala Arg Gly Thr
 65                  70                  75                  80

Ala Ile Thr Val Val Ser Pro Ala Asp Gly Leu Glu Gln Ile Ala Asn
                 85                  90                  95

Pro Phe Ala Thr Gln Glu Glu Glu
            100
```

(2) INFORMATION FOR SEQ ID NO:6:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 1078051

(xi) SEQUENCE DESCRIPTION: SEQ ID NO:6:

```
Met His Gln Gln His Ser Gln Arg Lys Lys Phe Glu Gly Pro Lys Arg
 1               5                  10                  15

Glu Ala Ile Leu Asp Leu Ala Lys Tyr Lys Asp Ser Lys Ile Arg Val
             20                  25                  30

Lys Leu Met Gly Gly Lys Leu Val Ile Gly Val Leu Lys Gly Tyr Asp
         35                  40                  45

Gln Leu Met Asn Leu Val Leu Asp Asp Thr Val Glu Tyr Met Ser Asn
 50                  55                  60

Pro Asp Asp Glu Asn Asn Thr Glu Leu Ile Ser Lys Asn Ala Arg Lys
 65                  70                  75                  80

Leu Gly Leu Thr Val Ile Arg Gly Thr Ile Leu Val Ser Leu Ser Ser
                 85                  90                  95

Ala Glu Gly Ser Asp Val Leu Tyr Met Gln Lys
            100                 105
```

(2) INFORMATION FOR SEQ ID NO:7:

(i) SEQUENCE CHARACTERISTICS:
        (A) LENGTH: 76 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 806566

(xi) SEQUENCE DESCRIPTION: SEQ ID NO:7:

```
Met Ser Lys Ala His Pro Pro Glu Leu Lys Lys Phe Met Asp Lys Lys
1               5                   10                  15

Leu Ser Leu Lys Leu Asn Gly Gly Arg His Val Gln Gly Ile Leu Arg
                20                  25                  30

Gly Phe Asp Pro Phe Met Asn Leu Val Ile Asp Glu Cys Val Glu Met
            35                  40                  45

Ala Thr Ser Gly Gln Gln Asn Asn Ile Gly Met Val Val Ile Arg Gly
        50                  55                  60

Asn Ser Ile Ile Met Leu Glu Ala Leu Glu Arg Val
65                  70                  75
```

(2) INFORMATION FOR SEQ ID NO:8:

(i) SEQUENCE CHARACTERISTICS:
        (A) LENGTH: 95 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 602898

(xi) SEQUENCE DESCRIPTION: SEQ ID NO:8:

```
Met Leu Phe Phe Ser Phe Phe Lys Thr Leu Val Asp Gln Glu Val Val
1               5                   10                  15

Val Glu Leu Lys Asn Asp Ile Glu Ile Lys Gly Thr Leu Gln Ser Val
                20                  25                  30

Asp Gln Phe Leu Asn Leu Lys Leu Asp Asn Ile Ser Cys Thr Asp Glu
            35                  40                  45

Lys Lys Tyr Pro His Leu Gly Ser Val Arg Asn Ile Phe Ile Arg Gly
        50                  55                  60

Ser Thr Val Arg Tyr Val Tyr Leu Asn Lys Asn Met Val Asp Thr Asn
65                  70                  75                  80

Leu Leu Gln Asp Ala Thr Arg Arg Glu Val Met Thr Glu Arg Lys
                85                  90                  95
```